United States Patent [19]
Penrose

[11] Patent Number: 5,897,513
[45] Date of Patent: Apr. 27, 1999

[54] ORTHOPAEDIC SPLINTING MATERIAL

[75] Inventor: Jane Edith Penrose, Skipton, United Kingdom

[73] Assignee: Smith & Nephew plc, London, United Kingdom

[21] Appl. No.: 08/776,434

[22] PCT Filed: Jul. 28, 1995

[86] PCT No.: PCT/GB95/01770

§ 371 Date: May 21, 1997

§ 102(e) Date: May 21, 1997

[87] PCT Pub. No.: WO96/04023

PCT Pub. Date: Feb. 15, 1996

[30] Foreign Application Priority Data

Jul. 29, 1994 [GB] United Kingdom ............... 9415371

[51] Int. Cl.$^6$ ....................................... A61L 15/07
[52] U.S. Cl. ..................................... 602/6; 602/8
[58] Field of Search .............................. 602/6, 8

[56] References Cited

U.S. PATENT DOCUMENTS 3,847,655  11/1974  Crimmel et al. ................. 442/63
5,088,484   2/1992  Freeman et al. ................. 602/44

FOREIGN PATENT DOCUMENTS

479269A1  4/1992  European Pat. Off. .
556058A1  8/1993  European Pat. Off. .
 9304709  3/1993  WIPO .

Primary Examiner—Richard J. Apley
Assistant Examiner—Kim M. Lee
Attorney, Agent, or Firm—Larson & Taylor

[57] ABSTRACT

A colored orthopedic splinting material comprising a glass fiber substrate and a hardenable resin wherein the individual filaments making up the substrate are colored.

10 Claims, No Drawings

ORTHOPAEDIC SPLINTING MATERIAL

BACKGROUND OF THE INVENTION

1. Field of the Invention

The present invention relates to a hardenable material which comprises a substrate carrying a hardenable resin, for example which hardens on contact with water. More specifically, this invention relates to a colored orthopaedic splinting material which carries a hardenable resin.

2. Description of Related Art

It is well established to use water hardenable isocyanate functional resins in orthopaedic splint bandages. Such bandages are disclosed in British Patent No. GB2216533.

For some considerable time now it has been desirable to use colored casting materials which includes for example solid colours, prints and multicolored decorations. Methods of colouring casting materials are disclosed in U.S. Pat. No. 5,476,438. However such casts suffer from the disadvantage that the colored prepolymers will readily stain other material with which they come into contact. Methods of overcoming this disadvantage are disclosed in European Patent Application No. 479269 and PCT Application No. WO93104709. Both applications generally relate to the manufacture of colored orthopaedic casts or multicolored orthopaedic casts by printing one or more pigments onto the surface of a knitted substrate which results in the coating or partial coating of some of the yarns but not the individual filaments. In addition, such printing techniques prove to be expensive in manufacture, inter alia, because of the need to clean machinery when changing production from one color to another. It is also a method which does not lend itself well to continuous production and generally requires a batch process.

A preferred material from which casting substrates can be formed are glass fibre yarns. Glass fibre yarns are conventionally manufactured by drawing molten glass through nozzles to form filaments. The filaments are cooled, sized and gathered to form glass fibre strands. The glass fibre strands are subsequently twisted and plied to form glass fibre yarns.

BRIEF SUMMARY OF THE INVENTION

Glass fibre yarns can be woven or knitted into casting substrates using similar processes as are used in textile operations.

In the electronics industry it has been known for nearly twenty years to coat wires with yarns manufactured from colored fibre glass filaments. Such yarns comprise individual filaments which are completely coated with a dye.

We have now found that such coloured yarns may also be used in the manufacture of colored substrates for use in orthopaedic casting. Thus such colored yarns may be used to produce colored, multicolored or patterned substrates for use in orthopaedic casting.

Thus it is novel to knit such colored yarns into a substrate or fabric which may be suitable for use as an orthopaedic splinting material.

According to the invention we provide a colored knitted or woven substrate comprising glass fibre yarns wherein the glass fibre yarns comprise a plurality of individual colored filaments. Preferably said substrate is a knitted substrate.

According to the invention we further provide a colored orthopaedic splinting material comprising a substrate carrying a hardenable resin wherein said substrate comprises glass fibre yarns characterised in that the glass fibre yarns comprise a plurality of individual colored filaments.

In a preferred embodiment of the invention the colored glass fibre substrate which comprises glass fibre yarns wherein the glass fibre yarns comprise a plurality of individual colored filaments is conformable.

Conformability of the substrate is achieved through knitting or weaving the colored glass fibre yarns, preferably the colored glass fibre yarns are knitted into a conformable, relatively stretchable substrate.

The substrate may be any colored glass fibre fabric which has the properties required for use as an orthopaedic bandage as regards to extensibility and strength. The glass fibre fabrics may be available in two knit-types namely a Raschel knit and a tricot knit.

The substrate is preferably in the form of a bandage but other forms of sheet materials, for example those to form slabs, are also envisaged. The glass fibre substrate may, in addition to glass fibre yarns, be composed of one or more natural or synthetic fibres conventionally used to form a plastic orthopaedic cast. The fibres can include cotton, nylon, polyester, acrylic and the like.

DETAILED DESCRIPTION OF PREFERRED EMBODIMENTS

According to the present invention we therefore provide a colored orthopaedic splinting material as hereinbefore described wherein the substrate is in the form of a bandage.

The coloured substrate of the invention is particularly advantageous in that it may carry a hardenable resin to produce an orthopaedic splinting material.

The substrate may carry the hardenable resin in a number of conventional ways per se and the substrate may for example be coated, impregnated or sprayed with the hardenable resin. In a preferred embodiment the substrate is coated with the hardenable resin.

The hardenable resin is preferably a water hardenable resin and especially an isocyanate functional resin. Aptly the resin used to coat the glass fibre substrate may be a cold water curable isocyanate terminated polyurethane prepolymer system. Among suitable polyurethane prepolymer systems are those identified in U.S. Pat. Nos. 4411262, 4427002, 4433680 and 4574793. Particularly preferred are those systems disclosed and claimed in U.S. Pat. Nos. 4,427,002 and 4,574,793. Particularly preferred resins are also those disclosed in British Patent No. GB2216533 and the whole of that document is intended to be incorporated herein by reference.

Thus according to the invention we further provide a colored orthopaedic splinting material as hereinbefore described comprising a substrate carrying a hardenable resin wherein the hardenable resin is an isocyanate functional resin.

In a further embodiment of the invention we provide a colored orthopaedic splinting material as hereinbefore described wherein the hardenable resin is a polyurethane prepolymer.

In a most preferred embodiment of the invention we provide a colored orthopaedic splinting material as hereinbefore described wherein the hardenable resin is a water hardenable resin.

Various known additives can be incorporated into the resin such as, for example, viscosity modifiers, uv stabilizers and/or antioxidants. Where desirable, various dyestuffs can also be incorporated into the resin in order to provide different colour effects for the resulting cast. The invention is also particularly useful in combination with resins other than the water curable polyurethane resins. For example, the casting materials of the invention can be used in combination with two component resin systems, such as epoxy based systems, unsaturated polyester systems and polyurethane systems where the isocyanate is maintained separately from the polyol. In such systems, the glass fibre substrate is maintained separately from one or both of the resin reactants until just prior to use. The glass fibre substrate may thus be packaged uncoated, or coated with only one component of the system and rolled into a roll. A separate portion of the pouch, or a separate pouch, contains either the second resin component or the liquid resin. Just prior to using the casting material to form a cast on the limb of a patient, the physician or cast technician applies the resin material or the second component thereof to the roll in order to initiate hardening of the resin.

The glass fibre filaments may be coloured by any conventional methods known per se. These include for example melting certain transition metal ions into a glass, the precipitation of coloured crystals which dissolve in glass at high temperatures and precipitate on cooling, the use of pigments, stains and dyes.

In a preferred embodiment of the present invention the glass fibre yarns comprise a plurality of individual colored filaments wherein the filaments are dyed. Any conventional dyeing method may be used. Preferably the colored glass fibre yarns are colorfast to light and have a high heat stability.

Any conventional dyes known to be suitable for application to glass fibre filaments may be used for example inorganic high temperature dyes or acrylic dyes. However, preferred dyes are those which do not interact with the resin and especially those which do not react within isocyanate resins. Preferred dyes are especially acrylic dyes.

The glass fibre substrate may consist of yarns comprising a plurality of individual colored filaments wherein the filaments may comprise a number of colors. Colored filaments may be mixed with filaments that have not been colored to achieve a desired shade or decorative effect for the substrate.

The use of differently colored filaments to prepare differently colored glass fibre yarns allows the incorporation of decorative patterns and motifs into the substrate. Two or more colored glass fibre yarns may be twisted together to produce multicoloured yarns.

Each glass fibre filament may be of a uniform color or may be colored with several colors or may be of a non-uniform color.

According to the invention we provide a method of preparation of a colored orthopaedic splinting material as hereinbefore described which comprises knitting or weaving a substrate from colored glass fibre filament yarns followed by coating or impregnating the substrate with a hardenable resin.

In a preferred embodiment of the invention we provide a method of preparation of a colored orthopaedic splinting material as hereinbefore described which comprises knitting a substrate from colored glass fibre filament yarns followed by coating the substrate with a hardenable resin.

Any suitable coating means can be used to coat the substrate with a resin including fixed doctor blade over flat bed, or roller and roller coating systems.

It is desirable that the resin during coating is protected from excessive moisture vapour. Suitable coating systems can be enclosed and can be conducted in an atmosphere free from excessive moisture vapour such as dry air, or inert gases for example carbon dioxide or nitrogen.

In a preferred continuous process the resin in liquid form is coated on to a length of the substrate by means of a blade over flat bed and the coated substrate by means of a blade over flat bed and the coated substrate dried, if necessary. The coated substrate can then be split into suitable sized strips and rolled up into bandages.

The amount of resin on the substrate should be sufficient to ensure that the resultant splint has adequate strength. Suitable amounts have been found to be 50 to 500 $gm^2$, preferably 100 to 305 $g/m^2$, for example 200 $g/m^2$, 250 $g/m^2$ or 300 $g/m^2$.

Preferably, the splinting bandages should be protected during storage from water and excessive moisture vapour to prevent a premature setting taking place, the bandages can be conventionally packaged in heat sealed waterproof pouches such as metal foil polyethylene laminate or polyethylene pouches.

In use the splinting bandages may be brought into contact with water and wrapped around the injured part of the body. The splinting bandage has a working time which is sufficient to allow the bandage to be positioned, and a set time which is the time taken for the splinting material to become rigid. Favoured working times are 1 minute to 6 minutes and especially 2 minutes to 4 minutes. Favoured set times are 5 minutes to 30 minutes and especially 6 minutes to 15 minutes.

It is novel to use dyed fibre glass yarns in orthopaedic splinting materials. Thus according to the invention we provide the use of glass fibre yarns comprising a plurality of individual coloured filaments in the manufacture of a substrate for use in the preparation of a colored orthopaedic splint.

We further provide a method of forming a colored orthopaedic splint of the present invention which comprises positioning a splinting material about a member to be immobilized said splinting material being adapted to set by polymerisation of a hardenable resin and thereafter causing the material to set by curing the resin.

In a further embodiment we provide a method of forming a colored orthopaedic splint of the present invention which comprises positioning a splinting material about a body part to be immobilised said splinting material being adapted to set by polymerisation of a water hardenable resin and causing the splinting material to set by introducing water to the splinting material.

According to the present invention we in addition provide a method for treating a fracture of a body part which comprises applying a colored orthopaedic splinting material as hereinbefore described to said body part and causing the splinting material to set by curing the hardenable resin.

The present invention is advantageous in that it provides, inter alia, method for material colored hardenable orthopaedic materials which is less expensive or less messy than known methods.

Orthopaedic splints may be prepared which comprise yarns of a single colour or yarns of different colors may be knitted together to provide multicolored materials.

The dyed glass fibre yarns for use in the present invention are available from Polux Limited of Rochdale in the United Kingdom.

The invention will now be illustrated but in no way limited by the following Example.

EXAMPLE 1

A water curable polyurethane resin system comprising a polyurethane prepolymer described in U.S. No. 4,574,793 as prepolymer A and containing methane sulphonic acid as stabiliser and bis(2,6 dimethylmorpholino)diethyl ether as catalyst was coated onto an untreated coloured knitted glass fibre fabric substrate comprising yarns of individual colored filaments using the process described in U.S. Pat. No. 4,427,002. The resin-coated colored glass fibre substrate was wound onto a master roll which is approximately 25 cm in width and is 500 m in length.

I claim:

1. A colored orthopaedic splinting material comprising a substrate carrying a hardenable resin wherein said substrate comprises yarns characterized in that the yarns comprise a plurality of individually colored filaments.

2. A colored orthopaedic material as claimed in claim 1 wherein the yarns comprise glass fibre yarns.

3. A colored orthopaedic splinting material as claimed in claim 1 characterized in that the hardenable resin comprises a water hardenable resin.

4. A method of forming a colored orthopaedic splint which comprises positioning a splinting material as claimed in claim 3 about a body part to be immobilized, said splinting material being adapted to set by polymerization of said water hardenable resin, and causing the splinting material to set by introducing water to the splinting material.

5. A colored orthopaedic splinting material as claimed in claim 1 characterized in that the hardenable resin comprises an isocyanate functional resin.

6. A colored orthopaedic splinting material as claimed in claim 1 characterized in that the hardenable resin comprises a polyurethane prepolymer.

7. A colored orthopaedic splinting material as claimed in claim 1 characterized in that the substrate is in the form of a bandage.

8. A colored orthopaedic splinting material as claimed in claim 1 characterized in that the filaments are dyed.

9. A method of preparation of a colored orthopaedic splinting material according to claim 1 which comprises knitting or weaving a substrate from colored filament yarns followed by coating or impregnating the substrate with a hardenable resin.

10. A method for treating a fracture of a body part which comprises applying a colored orthopaedic splinting material as claimed in claim 1 to the body part, and causing the splinting material to be set by curing the hardenable resin.

* * * * *